United States Patent
Breit et al.

(10) Patent No.: US 7,888,646 B2
(45) Date of Patent: Feb. 15, 2011

(54) SYSTEM AND METHOD FOR DETECTING CONTRABAND

(75) Inventors: Michael Breit, Munich (DE); Florian Krug, Munich (DE)

(73) Assignee: Morpho Detection, Inc., Newark, CA (US)

( * ) Notice: Subject to any disclaimer, the term of this patent is extended or adjusted under 35 U.S.C. 154(b) by 26 days.

(21) Appl. No.: 11/809,993

(22) Filed: Jun. 4, 2007

(65) Prior Publication Data

US 2008/0296501 A1   Dec. 4, 2008

(51) Int. Cl.
*G01J 5/02* (2006.01)
(52) U.S. Cl. .................. 250/341.1; 250/341.8
(58) Field of Classification Search .......... 250/341.1, 250/341.8
See application file for complete search history.

(56) References Cited

U.S. PATENT DOCUMENTS

| | | | |
|---|---|---|---|
| 5,692,029 A * | 11/1997 | Husseiny et al. ............... 378/88 |
| 5,710,430 A | 1/1998 | Nuss | |
| 6,078,047 A | 6/2000 | Mittleman et al. | |
| 6,605,808 B2 | 8/2003 | Mickan et al. | |
| 6,815,683 B2 | 11/2004 | Federici et al. | |
| 6,844,552 B2 | 1/2005 | Zhang et al. | |
| 6,909,095 B2 | 6/2005 | Tran et al. | |
| 6,957,099 B1 | 10/2005 | Arnone et al. | |
| 2005/0156110 A1 | 7/2005 | Crawely | |
| 2005/0242287 A1* | 11/2005 | Hakimi ................. 250/363.09 |
| 2006/0022140 A1 | 2/2006 | Connelly et al. | |
| 2006/0056586 A1 | 3/2006 | Uetake et al. | |
| 2006/0111619 A1 | 5/2006 | Castiglione et al. | |
| 2006/0214107 A1* | 9/2006 | Mueller ................. 250/341.8 |
| 2007/0114419 A1* | 5/2007 | Bastiaans et al. .......... 250/341.8 |
| 2007/0182528 A1* | 8/2007 | Breed et al. ................. 340/435 |
| 2010/0214150 A1* | 8/2010 | Lovberg et al. ............... 342/22 |

FOREIGN PATENT DOCUMENTS

| | | |
|---|---|---|
| EP | 0727671 A2 | 8/1996 |
| GB | 2405263 A | 2/2005 |
| GB | 2411093 A | 8/2005 |
| GB | 2418337 A | 3/2006 |
| WO | WO 00/50859 | 8/2000 |
| WO | WO 2004/072593 A2 | 8/2004 |
| WO | WO 2005/119214 A1 | 12/2005 |

OTHER PUBLICATIONS

Arttu Luukanen, Millimetrewave and Terahertz imaging in Security Technology, MilliLab, VTT, Jun. 11, 2005, (48 pages). Retrieved from the internet: URL: http://akseli.tekes.fi/opencms/opencms/OhjelmaPortaali/ohjelmat/ELMO/fi/Dokumenttiarkisto/Viestinta_ja_aktivointi/Seminaarit/ELMO_Results_Promotion/RFE_Luukanen.pdf.

(Continued)

*Primary Examiner*—David P Porta
*Assistant Examiner*—Mindy Vu
(74) *Attorney, Agent, or Firm*—Armstrong Teasdale LLP

(57) ABSTRACT

A technique is provided for detecting whether an object of interest is being carried by a subject. The technique includes coarsely scanning the subject with an electromagnetic radiation, measuring reflective intensity of radiation reflected from the subject, and detecting the presence or absence of the object of interest based upon the measured reflective intensity.

28 Claims, 9 Drawing Sheets

OTHER PUBLICATIONS

Chapter 3 THz Imaging, (28 pages), retrieved from the internet URL: http://thesis.library.adelaide.edu.au/uploads/approved/adt-SUA20050502.150032/public/04chapter3.pdf.

Thursday Afternoon / CLEO 2001 / 439, (2 pages), retrieved from the internet URL: http://ieeexplore.ieee.org/iel5/7534/20509/00948016.pdf?arnumber=948016.

Adrian Dobroiu, Masatsugu Yamashita, Yuichi N. Ohshima, Yasuyuki Morita, Chiko Otani, and Kodo Kawase, Terahertz imaging system based on a backward-wave oscillator, Applied Optics—vol. 43, No. 30—Oct. 20, 2004, (10 pages), retrieved from the internet URL: http://mtinstruments.com/thzresources/BWO%20THz%20Imaging.pdf.

Maya Gupta, Daniel Mittleman, Richard Baraniuk, Imaging with THz Radiation, (6 Pages), retrieved from the internet URL: http://idl.ee.washington.edu/publications/Hawaiipaper.pdf.

John F Federici et al., THz imaging and sensing for security applications—explosives, weapons and drugs, Institute of Physics Publishing, Semiconductor Science and Technology, Semicond. Sci. Technol. 20 (2005) S266-S280 doi:10.1088/0268-1242/20/7/018, 0268-1242/05/070266+15$30.00 © 2005 IOP Publishing Ltd Printed in the UK, (15 pages), retrieved from the internet URL: http://web.njit.edu/~federici/Research/THz/sst5_7_018.pdf.

* cited by examiner

SYSTEM AND METHOD FOR DETECTING CONTRABAND

BACKGROUND

The invention relates generally to techniques for detecting contraband and, more particularly, to techniques for remotely detecting contraband using electromagnetic radiation in the terahertz range.

A wide variety of inspection systems are employed at various public or private installations, such as airports, for screenings persons, luggage, packages and cargo, to detect the presence of contraband (e.g., weapons, explosives and drugs). Such systems include metal detectors, X-ray based inspection systems, nuclear magnetic resonance based inspection systems, nuclear quadruple resonance based inspection systems, and so forth. These inspection systems have one or more of various limitations such as low reliability in detecting explosives and drugs (leading to high rates of false alarms), health risk to screeners and those being screened due to exposure to harmful radiation, long screening time (leading to decreased throughput at checkpoints), and so forth.

Electromagnetic radiation in the terahertz range (about 0.1 terahertz to 10 terahertz), or terahertz radiation, is now being used in the field of contraband detection. Terahertz radiation easily penetrates clothes, cardboard, leather and other non-conductive (non-metallic) materials and poses minimal health risk to subjects being scanned. Moreover, a wide variety of contraband, such as explosives, drugs, chemical and biological agents, and so forth, show strong spectroscopic signatures in the terahertz range. These unique properties offer significant advantages in the field of contraband detection. However, known terahertz inspection systems are of limited practical utility because of their high cost and limited range of scanning. Additionally, known terahertz inspection systems require lengthy scan times per person or per piece of baggage, thereby reducing the throughput and causing inconvenience to those being screened. The complicated detection schemes (such as homodyne or heterodyne detection schemes, or time domain spectroscopic detection techniques that need advanced data analysis to alert) or sophisticated image generation procedures further increase the time required for detecting contraband or otherwise clearing a person or parcel.

It is therefore desirable to provide an efficient, reliable, and cost-effective inspection system for remote detection of contraband. It is also desirable to provide inspection systems that enable rapid scanning of the subject.

BRIEF DESCRIPTION

Briefly, in accordance with one aspect of the present technique, a method is provided for detecting whether an object of interest is being carried by a subject. The method provides for coarsely scanning the subject with an electromagnetic radiation, measuring reflective intensity of radiation reflected from the subject, and detecting the presence or absence of the object of interest based upon the measured reflective intensity. Systems that afford such functionality may be provided by the present technique.

In accordance with another aspect of the present technique, a method is provided for detecting a presence or absence an object of interest. The method provides for coarsely scanning a region of interest with an electromagnetic radiation in a terahertz range while selecting different frequencies of the electromagnetic radiation. The electromagnetic radiation may have a spot size of at least 1 centimeter at a predetermined scanning distance. The method also provides for measuring reflective intensity of radiation reflected from the scanned region, and detecting the presence or absence of the object of interest within the region of interest based upon the measured reflective intensity. Here again, systems affording such functionality may be provided by the present technique.

In accordance with a further aspect of the present technique, a system is provided for detecting whether an object of interest is being carried by a subject. The system includes a source configured to generate electromagnetic radiation in a terahertz range, an optical scanner configured to coarsely scan a region of interest within the subject with the generated electromagnetic radiation, and a detection subsystem configured to detect radiation reflected from the scanned region, measure reflective intensity of the reflected radiation, and detect the presence or absence of the object of interest within the region of interest based upon the measured reflective intensity.

These and other advantages and features will be more readily understood from the following detailed description of preferred embodiments of the invention that is provided in connection with the accompanying drawings.

DRAWINGS

DETAILED DESCRIPTION

The present techniques are generally directed to remote detection of contraband using terahertz radiation via spectroscopy. Such techniques may be useful in a variety of applications that require efficient, reliable, cost-effective, and rapid screening/inspection of persons, luggage, packages or cargo. Although examples are provide herein in the context of explosives detection using terahertz radiation, one of ordinary skill in the art will readily comprehend that the application of these techniques in other contexts, such as for drug detection using electromagnetic radiation in other ranges, may be within the scope of the invention.

It should be noted that reference is made herein to a scanned "subject". The use of the term is not intended to limit the scope of the appended claims and may broadly indicate a human, an animal, a sealed package, luggage such as a briefcase or a suitcase, a carton, or a cargo container that may be employed to carry an object of interest such as explosives, drugs or weapons. In general, the term may include any article, system, vehicle, or support in which or on which contraband may be placed.

Figure 1:
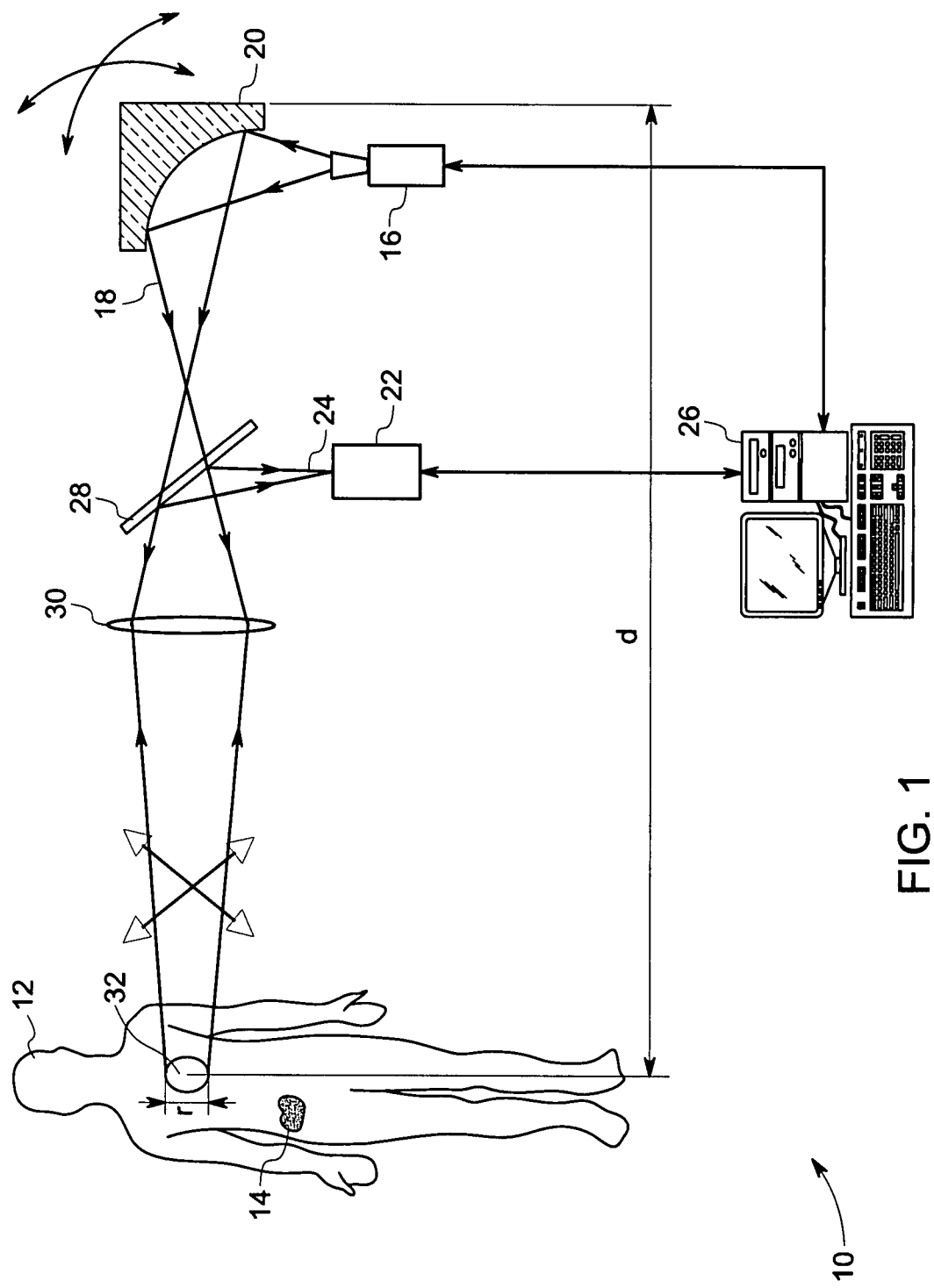
FIG. 1 is a schematic diagram of an inspection system for remotely examining a subject using electromagnetic radiation in accordance with an embodiment of the invention.
Figure 2:
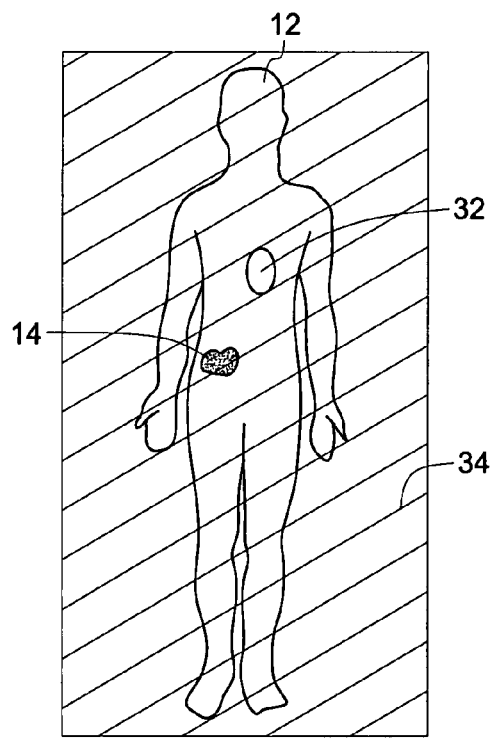
FIGS. 2-5 depict a subject being scanned via the inspection system of FIG. 1 from different scan directions in accordance with an embodiment of the invention.
Figure 3:
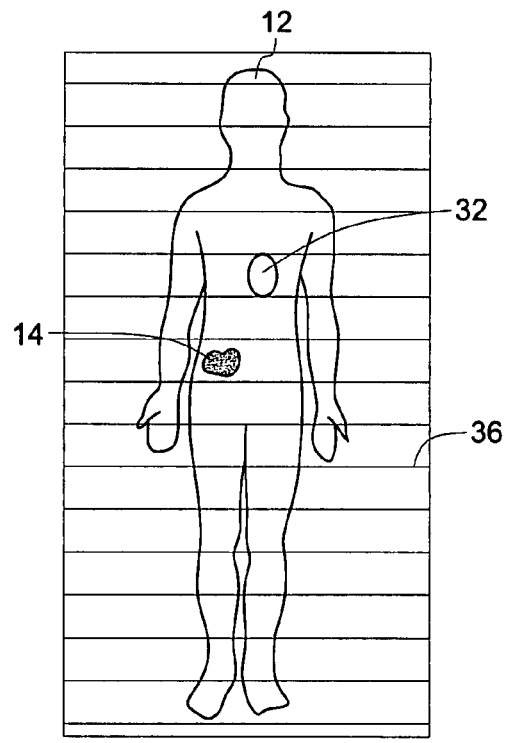
Figure 4:
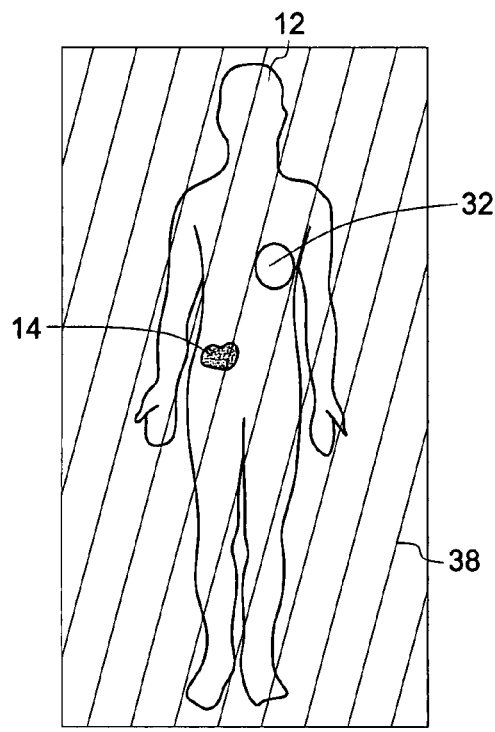

Referring now to FIG. 1, a schematic diagram of an exemplary inspection system 10 is illustrated. The system 10 is configured to remotely examine a subject 12 using electromagnetic radiation for detecting the presence of an object of interest 14 carried by the subject 12. The object of interest 14 may be contraband concealed on or in the subject 12.

The system 10 includes one or more sources 16 configured to generate electromagnetic radiation 18 and an optical scanner 20 configured to scan the subject 12 with the generated electromagnetic radiation 18. In certain embodiments, the generated electromagnetic radiation may be in a range of about 0.1 terahertz to about 10 terahertz (terahertz radiation). Alternatively, in certain embodiments the generated electromagnetic radiation may be in a range of about 10 gigahertz to about 100 gigahertz (millimeter waves). Further, in certain embodiments the optical scanner 20 may be a movable parabolic scanning mirror configured to scan the subject 12 in a circular pattern or other pattern. As will be appreciated by those skilled in the art, in certain embodiments the optical scanner 20 may include two or more scanning mirrors configured to scan the subject 12 along two or more axis respectively. The system 10 further includes a detection subsystem 22 configured to detect radiation 24 reflected from the subject 12, measure the reflective intensity of the reflected radiation 24, and detect the presence of the object of interest 14 based upon the measured reflective intensity. A control device 26 controls the source 16 and the detector subsystem 22. In certain embodiments, the control device 26 activates the source 16, synchronizes the detector subsystem 22 with the source 16 to enable frequency dependent detection, and generates a flag and/or an alarm upon detecting the presence of the object of interest 14.

Figure 5:
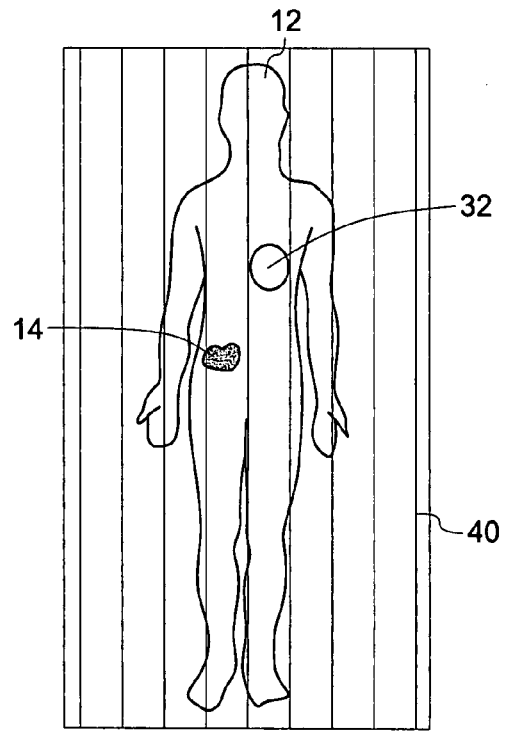

The system 10 further includes one or more optical devices such as a polarizer 28, a lens 30, a reflecting surface, and so forth to focus the generated radiation 18 on the subject 12 and reflected radiation 24 on the detection subsystem 22. As will be appreciated by one skilled in the art, the optical scanner 20 and the associated optical devices 28, 30 may be configured to scan the subject 12 via a variety of scanning schemes. For example, the optical scanner 20 is configured to coarsely scan the subject 12 by focusing the electromagnetic radiation 18 such that the electromagnetic radiation 18 forms a scanning spot 32 at a scanned distance "d" from the optical scanner 20. The optical scanner 20 may illuminate the spot 32 and move the spot 32 to scan the entire subject. The size of the scanning spot 32 may be varied depending upon the required resolution, sensitivity of detection, and scan time. As will be appreciated by those skilled in the art, the larger the size of the scanning spot 32, the less time is required to scan the subject 12. Thus, broadly focusing the radiation leads to a large spot size and enables rapid scanning of the subject 12 since high spatial resolution is not needed. In certain embodiments, the size of the spot "r" is at least 1 centimeter in diameter at the scanned distance. Alternatively, in certain embodiments, the size of the spot "r" may be greater than 5 centimeters in diameter at the scanned distance. Again, in certain embodiments, the size of the spot "r" may be greater than 15 centimeters in diameter at the scanned distance. As noted above, beam forming resulting in large spots allows for very rapid scan modes. Further, it should be noted that the optical scanner 20 may be configured to scan the subject 12 in any scan directions. For example, as illustrated in FIGS. 2-5, the subject 12 may be scanned via a progressive, generally slanting horizontal beam movement, as indicated by reference numeral 34 (FIG. 2); a progressive generally horizontal beam movement, as indicated by reference numeral 36 (FIG. 3); a progressive generally slanting vertical beam movement 38 (FIG. 4); or a progressive generally vertical beam movement 40 (FIG. 5).

Figure 6:
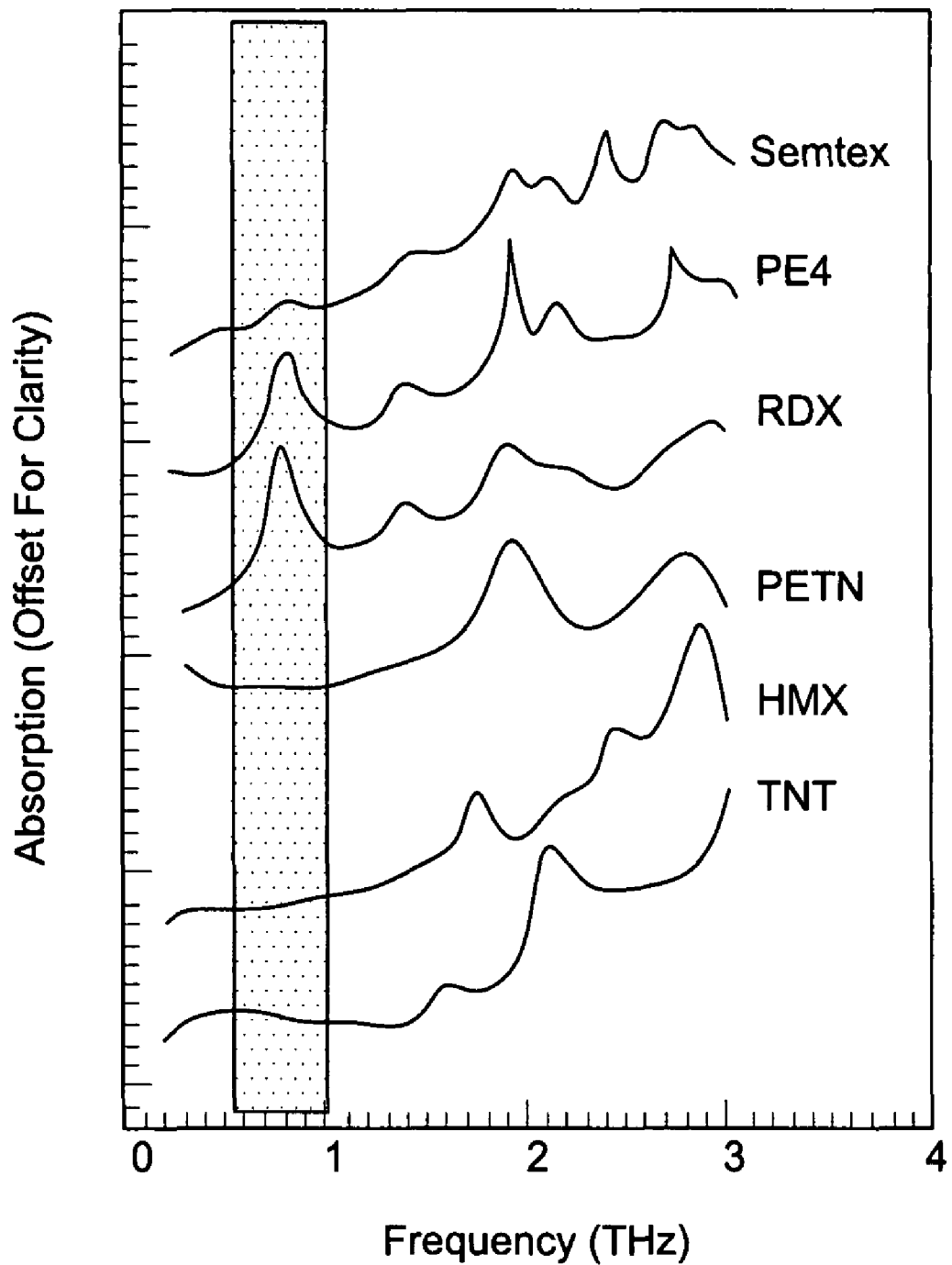
FIG. 6 depicts absorption spectra of various explosives in the terahertz range.
Figure 7:
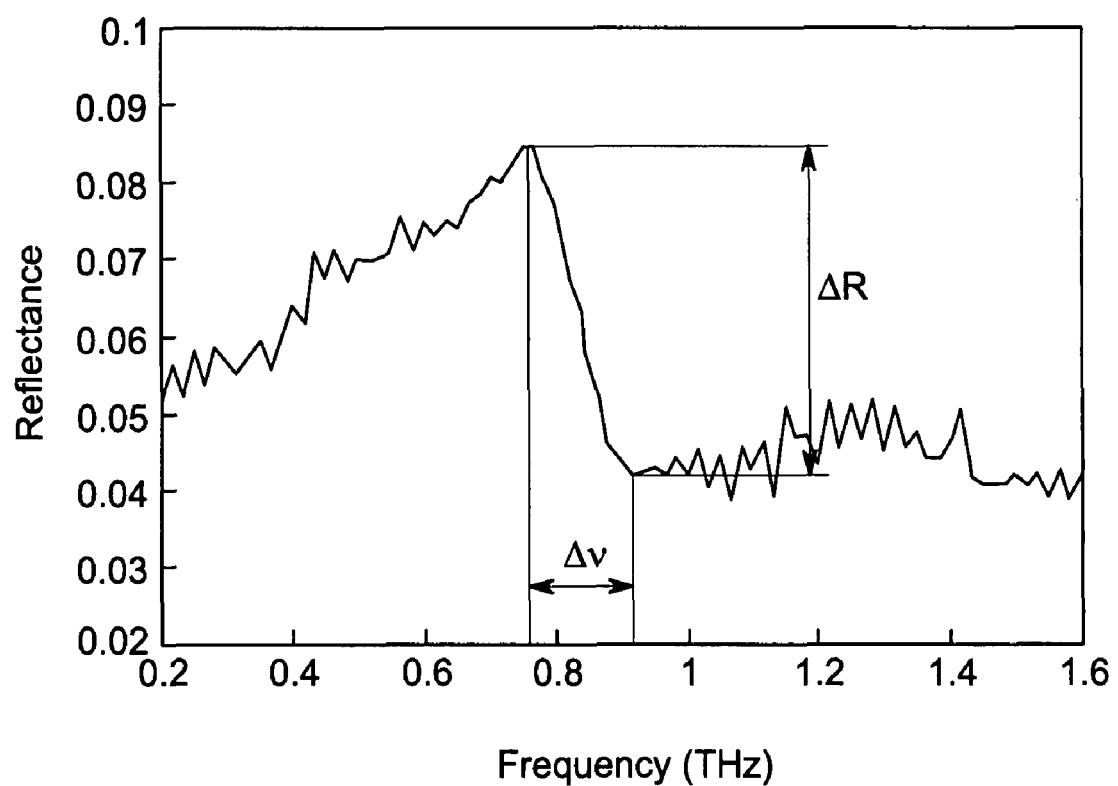
FIG. 7 depicts a reflectivity change occurring in the measured reflection spectrum of an explosive material when scanned with electromagnetic radiation in the terahertz range.

As will be appreciated by those skilled in the art, the detection subsystem 22 is configured to detect the presence of the object of interest 14 by detecting the presence of spectroscopic signatures (characteristic reflection and/or absorption spectra) of the respective object of interest 14 from the measured reflective intensity. For example, in certain embodiments, the object of interest includes an explosive material. The detection of these explosive materials is based upon a spectroscopic signature (characteristic absorption and/or reflection spectra) of the explosive material. A wide variety of explosives show strong spectroscopic signatures in the terahertz range. FIG. 6 illustrates absorption spectra of various explosives in this range. As shown, explosives such as TNT, HMX, PETN, RDX, PE4, Semtex and others have characteristic reflection and absorption spectra in the range of about 0.3 to about 3 terahertz that are easily distinguishable from other materials, such as human skin. A significant change of the signal indicates with very high probability the presence of explosive materials. It should be noted that the signal change is proportional to the reflectivity/absorbance change ($\Delta R/\Delta A$) in a specific frequency interval ($\Delta v$) and therefore is a significant measure of explosive materials leading to identification of contraband with very low false alarm rates. For example, as illustrated in FIG. 7, a significant reflectivity change of about 50% occurs in the measured reflection spectrum of SX2 (plastic sheet explosive material) in a distance of 1 meter within a small frequency band of about 150 gigahertz.

By comparing measured reflective intensity of the reflected radiation 24 with the known calibration spectra, the presence of explosives, drugs or other contraband may be identified. As will be appreciated by those skilled in the art, the detection subsystem 22 or the control device 26 may maintain a look-up table of known explosives and drugs along with their known characteristic reflection and absorption spectra (spectroscopic signatures) in the terahertz range. The measured reflective intensity will therefore be mapped onto some signature in the look-up table if the respective explosive or drug is present. In other words, the inspection system 10 uses a priori information of explosive materials and drugs by their spectral response in the terahertz regime. Additionally, since metals are relatively opaque to transmission of terahertz radiation and have a roughly constant reflection spectrum, metal weapons such as handguns and knives may also be identified by terahertz radiation.

The detection subsystem 22 may include any indirect broadband detectors, such as Golay cell broadband detectors, cryogenically cooled bolometers (e.g., helium cooled silicon bolometer), antennae coupled bolometers, pyroelectric broadband detectors, and so forth. These detectors permit spectroscopic identification or sensing of explosives and drugs with ultra broadband sensitivity. It should be noted that the employed detector may be synchronized with the source to enable frequency dependent detection.

The one or more sources 16 may be any sweepable ultra-broadband high-power source, such as a backward wave oscillator (BWO) source, a quantum cascading laser (QCL) source, a multiplier chain source, or a gas laser source. As will be appreciated by one skilled in the art, the strong absorption at about 0.8 terahertz may be reached with state of the art BWO sources. Moreover, the high power source enables long-range spectroscopic sensing (remote or standoff detection). In certain embodiments, the source 16 may be configured to generate electromagnetic radiation at continuous frequencies in the terahertz range. In other words, the source is in continuous tuning mode and the delivered frequency range is large enough to resolve the spectral features of the contraband completely. The specific shape of the measured signal may then be compared with the shape of the known spectral features of contraband to identify them. For example, BWO sources may sweep over a full spectral peek of explosive materials.

Alternatively, one or more sources 16 may be tuned to generate electromagnetic radiation at multiple discrete frequencies in the terahertz range. In one embodiment, several discrete sources (e.g., QCL sources, multiplier chain sources and so forth) may be employed that may be switched by shutters. The inspection system 10 uses a priori information of sources (the characteristic frequency difference between the sources) to measure expected changes of reflection of the explosives in the signal. Further, each of the multiple discrete frequencies is selected based upon a known spectroscopic signature (characteristic reflection and/or absorption spectra) of the object of interest 14. Thus, the detector subsystem 22 measures reflective intensity of the reflected signals at few discrete frequencies close to the spectral signatures of the explosives and drugs. The source 16 therefore behaves as a narrowband source at any particular point of time since it does not generate electromagnetic radiation at continuous frequencies ranging the full spectrum. In other words, the source 16 can sweep specific frequencies such that some of the frequencies correspond to the frequency of explosive signature. By sweeping such specific frequencies, the detector will receive and read these frequencies. Depending upon the type of explosives or drugs carried by the subject 12, the explosive or drug may appear at certain frequencies and may not appear at other frequencies. Thus, the reflective intensity measurement is done for an entire region of the subject or a region within the subject 12 towards which a selected narrow bandwidth of radiation is directed or focused.

Figure 8:
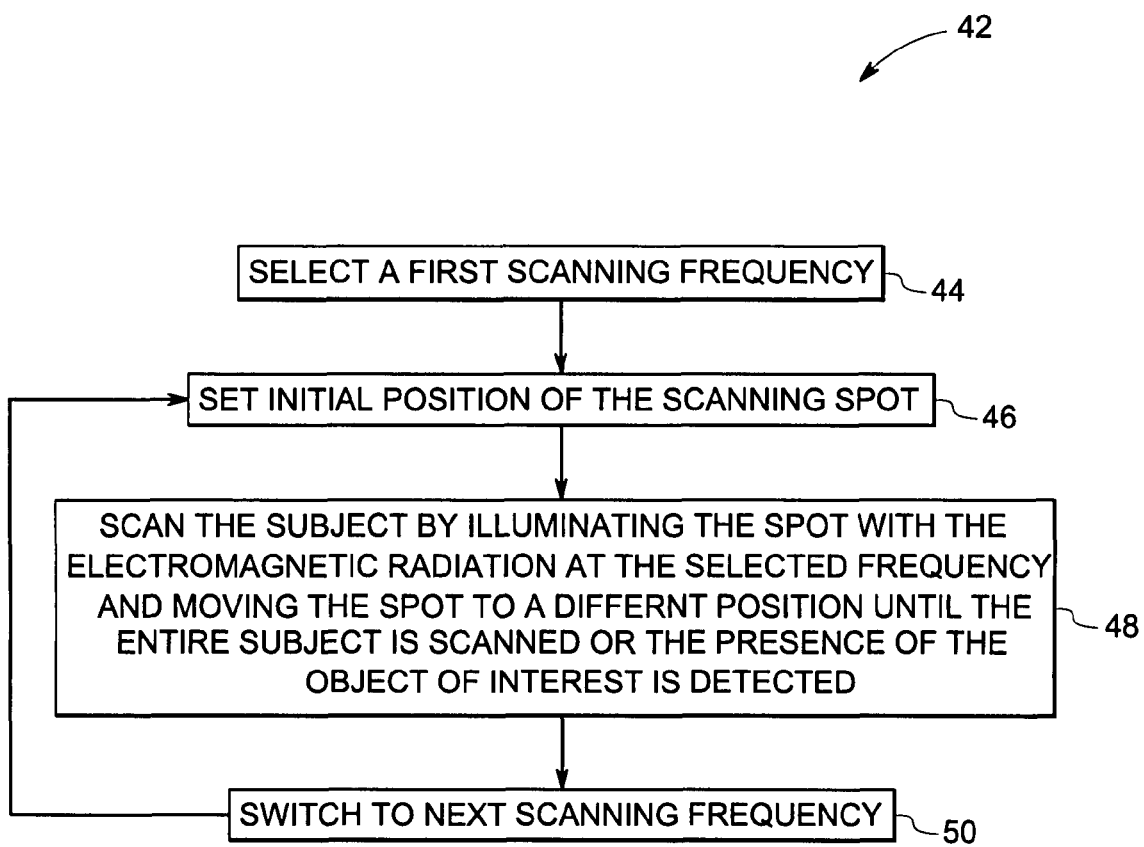
FIG. 8 depicts a control scheme for scanning a subject at multiple frequencies via the inspection system of FIG. 1 in accordance with an embodiment of the invention.
Figure 9:
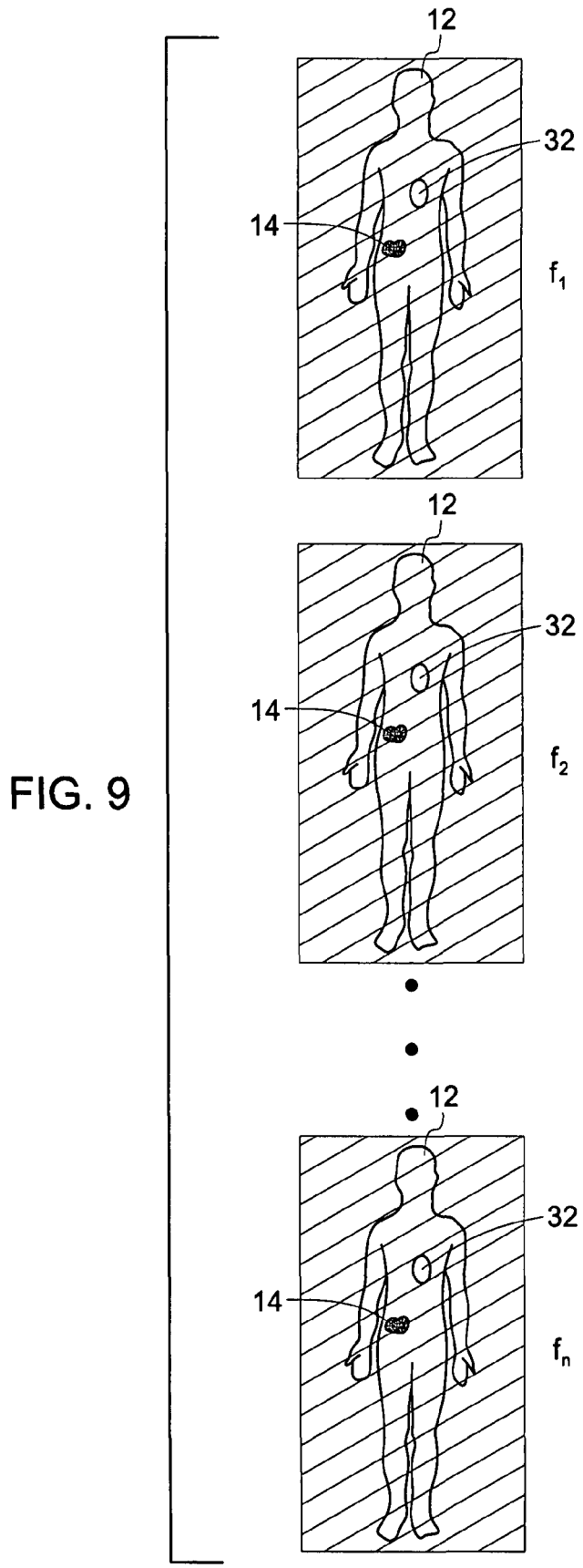
FIG. 9 depicts a subject being scanned at multiple frequencies via the control scheme of FIG. 8.

As will be appreciated by those skilled in the art, the optical scanner 20 is configured to coarsely scan the subject 12 at each of the selected multiple frequencies. It should be noted that scanning the subject 12 may be done in various ways, two of which will be described in greater detail below. In certain embodiments, the entire subject 12 may be scanned at one selected frequency and then with a next selected frequency as illustrated in FIGS. 8 and 9. FIG. 8 illustrates a control scheme 42 for scanning the subject 12 as stated above. The control scheme 42 includes selecting a first scanning frequency at step 44, setting an initial position of the spot for scanning the subject at step 46, scanning the subject 12 by illuminating the spot with the electromagnetic radiation at the selected frequency, and moving the spot to a different position until the entire subject 12 is scanned or the presence of the object of interest 14 is detected (or the subject 12 is cleared at that frequency) at step 48. The system may then switch to next scanning frequency at step 50, and steps 46 to 50 are repeated until the subject 12 is scanned at all scanning frequencies. FIG. 9 illustrates the subject 12 being scanned at multiple frequencies $f_1, f_2 \ldots f_n$ via the control scheme 42 described above.

Figure 10:
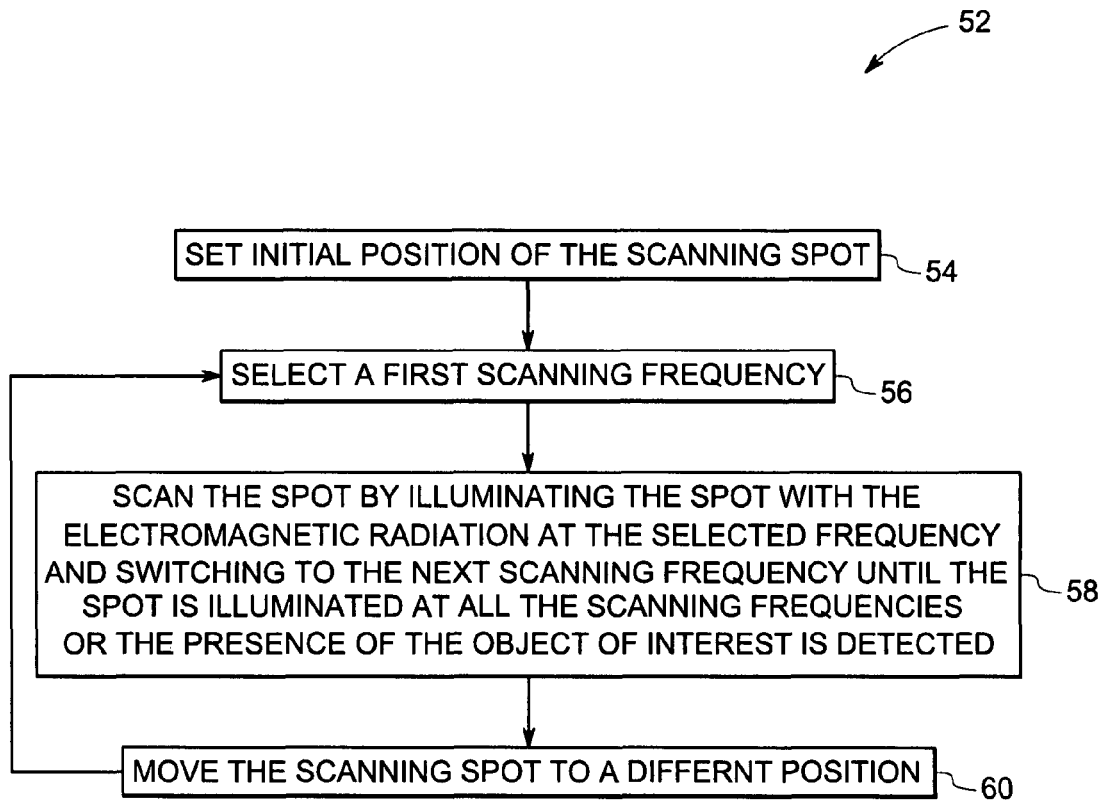
FIG. 10 depicts a control scheme for scanning a subject at multiple frequencies via the inspection system of FIG. 1 in accordance with an embodiment of the invention.
Figure 11:
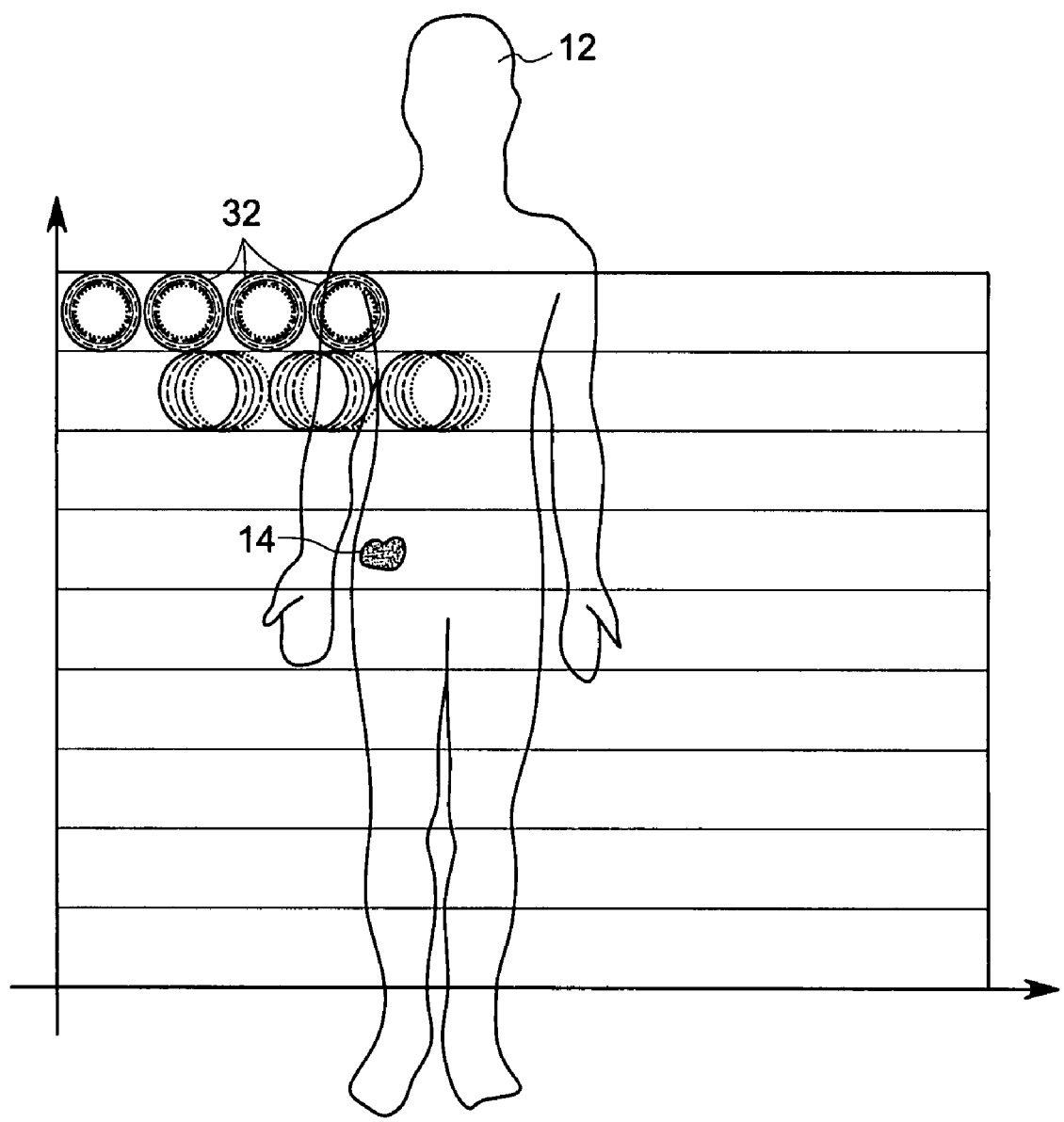
FIG. 11 depicts a subject being scanned at multiple frequencies via the control scheme of FIG. 10.

Alternatively, in certain embodiments each region of the subject 12 is scanned at multiple frequencies before moving on (or too far) to a next region, as illustrated in FIGS. 10 and 11. FIG. 10 illustrates a control scheme 52 for scanning the subject 12 as stated above. The control scheme 52 includes setting an initial position of the spot for scanning the subject 12 at step 54, selecting a first scanning frequency at step 56, and scanning the spot by illuminating the spot with the electromagnetic radiation at the selected frequency and switching to the next scanning frequency until the spot (or the general area) is illuminated at all scanning frequencies or the presence of the object of interest 14 is detected at step 58. The spot may then be moved to a different position at step 60 and steps 56 to 60 are repeated until the entire subject 12 is scanned. FIG. 11 illustrates the subject 12 being scanned at multiple frequencies via the control scheme 52 described with reference to FIG. 9.

It should be noted that the optical scanner 20 is configured to scan the subject 12 continuously or intermittently as illustrated in FIG. 11. For example, the spot position may or may not move while the electromagnetic radiation at the next selected frequency is being focused at the subject 12. Further, as will be appreciated by those skilled in the art, in certain embodiments, the source 16 is configured to switch between the multiple frequencies at a rate faster than the coarse scanning rate of the optical scanner 20 (i.e., the rate of movement of the spot). It should be noted that, in certain embodiments, the source 16 may sweep frequencies in the microsecond range. It may be desirable, therefore, to move the optical scanner 20 (course scanning rate) slower than the sweeping rate of the source 16. This is particularly important where each spot is scanned at multiple frequencies before scanning next spot.

Further, in certain embodiments an additional source 16 may be employed for generating electromagnetic radiation in a range of about 10 gigahertz to about 100 gigahertz (millimeter waves). The subject 12 is coarsely scanned with the millimeter waves to identify a region of interest within the subject 12. Alternatively, in certain embodiments, a millimeter wave based inspection system may be employed to do a preliminary scan to identify the region of interest. The identified region of interest may then be scanned with the electromagnetic radiation in terahertz range. Thus, detecting the presence of the object of interest 14 comprises identifying a region of interest within the subject 12 and scanning the region of interest at multiple frequencies of the electromagnetic radiation in the terahertz range to detect the object of interest 14. As will be appreciated by those skilled in the art, in certain embodiments, a single terahertz beam can be guided through to do a multi-spectral measurement at an identified region of interest. Here, only a single spot terahertz measurement is necessary.

Figure 12:
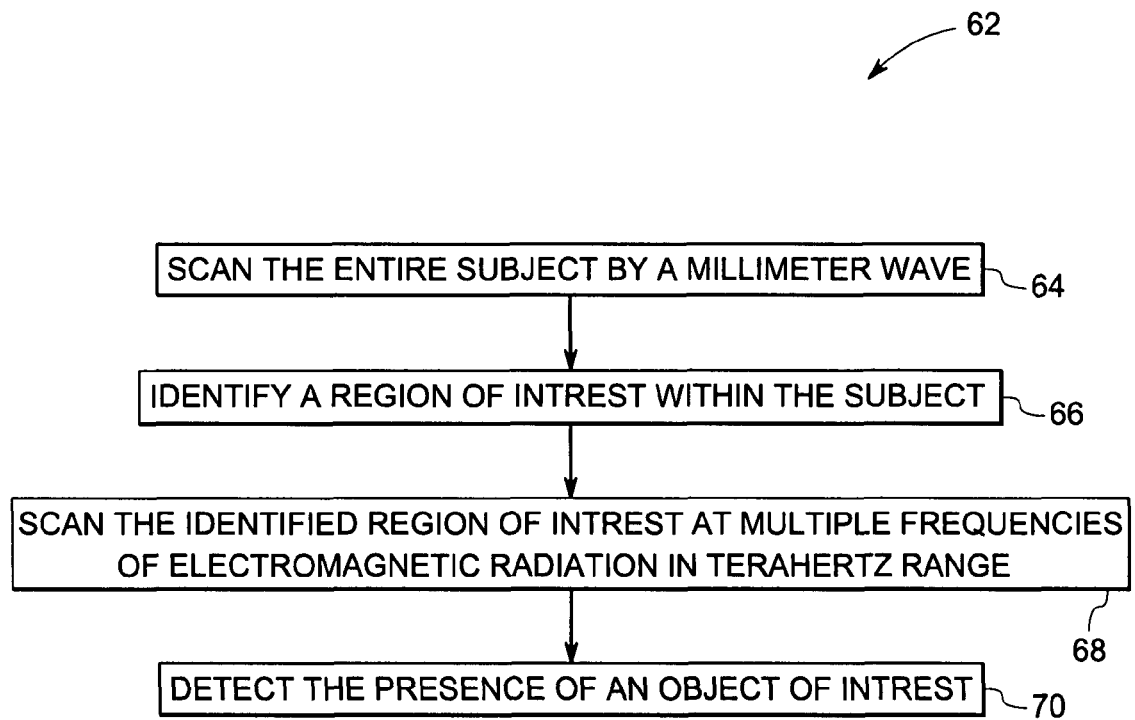
FIG. 12 depicts a control scheme for scanning a subject via the inspection system of FIG. 1 by employing an additional source of electromagnetic radiation in accordance with an embodiment of the invention.

FIG. 12 illustrates a control scheme 62 for detecting the object of interest 14 by scanning the subject 12 as stated above. The control scheme 62 includes coarsely scanning the entire subject 12 by a millimeter wave at step 64, identifying a region of interest within the subject 12 that needs further investigation at step 66, scanning the identified region of interest at multiple frequencies of the electromagnetic radiation in terahertz range at step 68, and detecting the presence of the object of interest 14 within the identified region of interest at step 70.

The techniques described in the various embodiments discussed herein enable efficient, reliable, cost-effective, and remote detection of contraband. Broad focusing of the electromagnetic radiation results in large spot size and hence enables fast scan modes. Employing broadband detectors and scanning the subject with large spot size of the electromagnetic radiation enables near real time spatial and spectral scanning, thereby increasing throughput and decreasing the inconvenience caused during screening. The spectroscopic techniques for detecting just the trace of explosives and drugs ensure that no image is being generated, thereby reducing the detection time and leading to fast detection of explosives. In other words, the techniques described in the various embodiments discussed above enable near real time scan and detection of the contraband. The inspection system 10 can spatially and spectrally scan the subject and detect the presence of any contraband in near real time.

Additionally, the use of high power source enables standoff detection (long range detection). Terahertz spectroscopy makes use of the spectral "fingerprint signatures" that a wide variety of explosives and drugs show in this regime. This enables a very high probability of explosives detection and low false alarm rates. Moreover, the use of active indirect detection leads to cost optimization.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A method for detecting whether an object of interest is being carried by a subject, the method comprising:
    coarsely scanning the subject with an electromagnetic radiation using a plurality of frequencies of electromagnetic radiation generated by at least one of spectral tuning of a narrow band source and using multiple discrete frequency sources, wherein the frequencies are selected based upon a known spectroscopic signature of the object of interest;
    measuring reflective intensity of radiation reflected from the subject; and,
    without generating an image, detecting the presence or absence of the object of interest based upon the presence or absence of the known spectroscopic signature of the object of interest from the measured reflective intensity.

2. The method of claim 1, wherein said coarsely scanning comprises coarsely scanning with an electromagnetic radiation in a range of about 0.1 terahertz to about 10 terahertz.

3. The method of claim 1, wherein said coarsely scanning comprises scanning the subject with an electromagnetic radiation having a spot size of at least 1 centimeter at a predetermined scanning distance.

4. The method of claim 3, wherein the spot size is at least five centimeters at the scanning distance.

5. The method of claim 3, wherein the spot sizes more than 15 centimeters at the scanning distance.

6. The method of claim 1, wherein said coarsely scanning comprises switching between the plurality of frequencies at a rate faster than a rate of coarsely scanning.

7. The method of claim 1, wherein the electromagnetic radiation is in a range of about 10 gigahertz to 100 gigahertz.

8. The method of claim 7, wherein said detecting the presence of the object of interest comprises identifying a region of interest within the subject and scanning the region of interest at multiple frequencies of the electromagnetic radiation in the terahertz range to detect the object of interest.

9. The method of claim 1, wherein the object of interest includes an explosive material and wherein said detecting the presence or absence of the object of interest is based upon a spectroscopic signature of the explosive material.

10. The method of claim 1, wherein said coarsely scanning the subject comprises scanning the subject continuously or scanning the subject intermittently.

11. A method for detecting a presence or absence of an object of interest, the method comprising:
    coarsely scanning a region of interest with an electromagnetic radiation in the terahertz range while selecting different frequencies of the electromagnetic radiation generated by at least one of spectral tuning of a narrow band source and using multiple discrete frequency sources, the electromagnetic radiation having a spot size of at least 1 centimeter at a predetermined scanning distance;
    measuring reflective intensity of radiation reflected from the scanned region; and,
    without generating an image, detecting the presence or absence of the object of interest within the region of interest based upon the presence or absence of a spectroscopic signature of the object of interest from the measured reflective intensity.

12. The method of claim 11, comprising coarsely scanning a region with an electromagnetic radiation in a range of about 10 gigahertz to about 100 gigahertz to identify the region of interest within the region.

13. The method of claim 11, wherein the spot size is at least five centimeters at the scanning distance.

14. The method of claim 11, wherein the spot size is more than 15 centimeters at the scanning distance.

15. The method of claim 11, wherein each of the selected different frequencies is based upon a known spectroscopic signature of the object of interest.

16. A system for detecting whether an object of interest is being carried by a subject, the system comprising:
    a narrow band source configured to generate electromagnetic radiation by spectral tuning in terahertz range;
    an optical scanner configured to coarsely scan a region of interest within the subject with the generated electromagnetic radiation; and
    a detection subsystem configured to detect radiation reflected from the scanned region, measure reflective intensity of the reflected radiation, and, without generating an image, detect the presence or absence of the object of interest within the region of interest based upon the presence or absence of a spectroscopic signature of the object of interest from the measured reflective intensity.

17. The system of claim 16, wherein the source comprises a backward wave oscillator source, a quantum cascading laser source, a multiplier chain source, a gas laser source, or other sweepable ultra-broadband high-power source.

18. The system of claim 16, wherein the source is configured to generate electromagnetic radiation at multiple frequencies in the terahertz range and wherein the optical scanner is configured to coarsely scan the region of interest at the multiple frequencies of the electromagnetic radiation.

19. The system of claim 18, wherein each of the multiple frequencies is selected based upon a known spectroscopic signature of the object of interest.

20. The system of claim 18, wherein the source is configured to switch between the multiple frequencies at a rate faster than the coarse scanning rate of the optical scanner.

21. The system of claim 16, wherein the optical scanner is configured to scan the region of interest with the electromagnetic radiation having a spot size of at least one centimeter at a predetermined scanning distance.

22. The system of claim 21, wherein the spot size is at least five centimeters at the scanning distance.

23. The system of claim 21, wherein the spot size is more than 15 cm at the scanning distance.

24. The system of claim 16, wherein the optical scanner is configured to coarsely scan the region of interest continuously.

25. The system of claim 16, wherein the detection subsystem comprises a Golay cell broadband detector, a cryogenically cooled bolometer, an antenna coupled bolometer, a pyroelectric broadband detector, or other broadband detectors.

26. The system of claim 16, wherein the detector subsystem is synchronized with the source to enable frequency dependent detection.

27. The system of claim 16, further comprising another source for generating electromagnetic radiation in a range of about 10 gigahertz to about 100 gigahertz.

28. The system of claim 27, wherein the optical scanner is configured to coarsely scan the subject with the electromagnetic radiation in the range of about 10 gigahertz to about 100 gigahertz to identify the region of interest.

* * * * *